United States Patent [19]

Haigh

[11] Patent Number: 4,689,132
[45] Date of Patent: Aug. 25, 1987

[54] ETCHING CHARGE MEASUREMENT SYSTEM

[75] Inventor: Richard B. Haigh, Buchanan, Mich.
[73] Assignee: Leco Corporation, St. Joseph, Mich.
[21] Appl. No.: 833,134
[22] Filed: Feb. 24, 1986
[51] Int. Cl.[4] .................. C25D 17/00; C25F 3/02; C25F 7/00; G01N 21/85
[52] U.S. Cl. ................. 204/224 M; 204/228; 204/275; 356/410
[58] Field of Search ........... 204/129.2, 275, 224 M, 204/228; 356/409, 410, 412, 414; 436/73, 78

[56] References Cited

U.S. PATENT DOCUMENTS

| | | | |
|---|---|---|---|
| 2,744,061 | 5/1956 | De Ford et al. | 204/275 X |
| 3,189,533 | 6/1965 | Anscherlík | 204/275 X |
| 4,243,326 | 1/1981 | Yee | 356/414 |
| 4,533,642 | 8/1985 | Kelly | 436/78 |

FOREIGN PATENT DOCUMENTS 2527555 1/1976 Fed. Rep. of Germany ........ 436/78

Primary Examiner—Donald R. Valentine
Attorney, Agent, or Firm—Price, Heneveld, Cooper, DeWitt & Litton

[57] ABSTRACT

An analyzer for acid-soluble aluminum in a steel sample precisely controls the etching charge by monitoring the etching current level and integrating the current with time. Once a predetermined charge is reached, the etching current is terminated. In a preferred embodiment, the etching cell is stacked above the mixing and developing chamber such that etching fluid flow is by gravity between these elements.

20 Claims, 6 Drawing Figures

ETCHING CHARGE MEASUREMENT SYSTEM

BACKGROUND OF THE INVENTION

The present invention relates to the analysis of acid-soluble aluminum in a steel sample and particularly an analyzer and etching charge measurement system used for determining the acid-soluble aluminum content.

During the manufacturing of steel, it is desirable to monitor the aluminum content of the steel and particularly the acid-soluble aluminum content. A variety of prior techniques have been proposed including a system of electrolytically etching a sample as disclosed in U.S. Pat. No. 4,533,642, issued to J. Kelly on Aug. 6, 1985. In electro-chemical systems, the weight of a sample in solution can be accurately determined by electrolytically etching a sample with a known quantity of charge according to Faraday's Law. In the implementation of this system, a constant current source is coupled to etching electrodes for a predetermined time. It is assumed that the current remains constant with time during etching for estimating the charge applied to the specimen. The difficulty with this system is that the actual charge is not measured, and the current can vary with temperature of electrolyte, sample type and its surface characteristics. Thus, the weight of material etched is only predicted. Further, the equipment employed in this system requires the utilization of a peristaltic pump for the movement of the etching solution and reagents involved in the process. This construction requires a debubbling chamber to eliminate gas bubbles from the chemical mixture before being analyzed by a spectral photometer.

SUMMARY OF THE PRESENT INVENTION

The system of the present invention overcomes the difficulty of the prior art and provides an extremely accurate and fast analysis of acid-soluble aluminum in steel by providing an electrical circuit which monitors the etching current and a control system which terminates the etching current as soon as a predetermined charge has been reached. The amount of charge is selectable for providing different ranges of operation, and the system utilizes a unique combination of an electrolytic cell and a mixing and development chamber to eleminate the need for pumping chemicals between these elements and debubbling prior to analysis.

In a preferred embodiment of the present invention, a power supply is provided with means for selectively coupling the power supply to electrodes of an etching cell for providing etching current to the cell. Current sensing means are placed in series with the etching current flow path and is coupled to circuit means for detecting current and providing a time control for the application of the current. The electrical circuit includes means for integrating the current with time to determine when a predetermined amount of charge has been applied to a sample in the electrolytic cell and decoupling the power supply from the cell when such level has been reached.

The apparatus employed in connection with the system of the present invention includes an etching cell and mixing chamber with the etching cell positioned above the mixing chamber with a common fluid flow path and selectively actuated valve means for gravity draining the etching solution into the mixing and developing chamber for subsequent processing.

The vertical stacking of the etching and mixing chambers eliminates the need for the pumping of chemicals and debubbling. The lower mixing chamber includes a colorimeter which provides a signal output representative of the amount of dye chelated on the dissolved aluminum and therefore the amount of aluminum present in the sample.

Thus the system and method of the present invention provides an extremely accurate analyzer which efficiently handles the sample and reagents involved in the analysis process. These and other features, objects and advantages of the present invention will become apparent upon reading the following description thereof together with reference to the accompanying drawings in which:

IDETAILED DESCRIPTION OF THE PREFERRED EMBODIMENT

The system of the present invention provides both a unique circuit and method of determining the exact charge applied to a sample for the etching of acid-soluble aluminum in a metallic specimen as well as the equipment providing efficient etching, mixing and analysis of a specimen.

Figure 1:
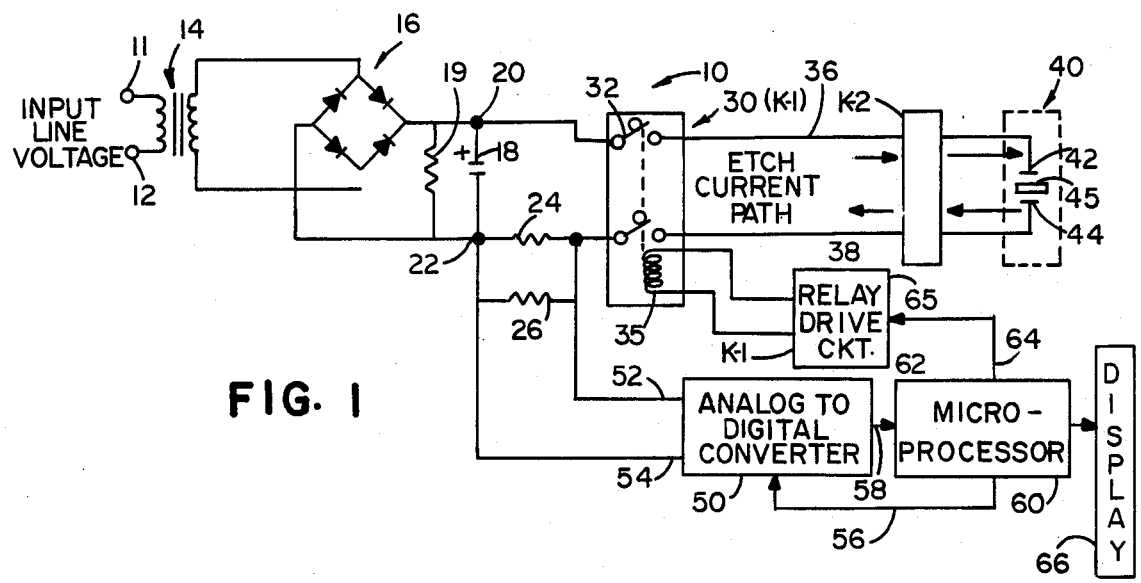
FIG. 1 is an electrical circuit diagram in block and schematic form of a system embodying the present invention.

Referring initially to FIG. 1, there is shown an electrical circuit 10 having a pair of input terminals 11 and 12 for coupling to an AC line supply with the terminals being coupled to the primary of a step down transformer 14 having a secondary winding coupled to input terminals of a full wave rectifier bridge 16. The output terminals of bridge 16 are coupled to a filter capacitor 18 and bypass resistor 19 in a conventional manner to provide an approximately +10 volt DC power supply at output terminal 20 of the power supply. As will be appreciated, the power supply voltage need not be regulated due to the sensing and monitoring of the current flowing through the etching cell and thus the voltage is not critical.

Output terminal 20 of the power supply is coupled to the positive electrode 42 of the etching chamber 40 by means of contact 32 of a first double-pole, single-throw relay 30 (also K-1 in FIGS. 1 and 5) and a closed first contact of a second double-pole, double-throw relay K-2. The lower contact 44 of etching cell 40 is coupled to the common terminal 22 of the power supply through a pair of parallel coupled 0.1 ohm resistors 24 and 26, conductive path 33 and the remaining closed contact of relay K-2. The contacts of relay K-2 are coupled in a conventional manner to selectively reverse the polarity of the voltage applied to the etching cell for cleaning the cathode or lower electrode 44 of cell 40 as described below.

Figure 6:
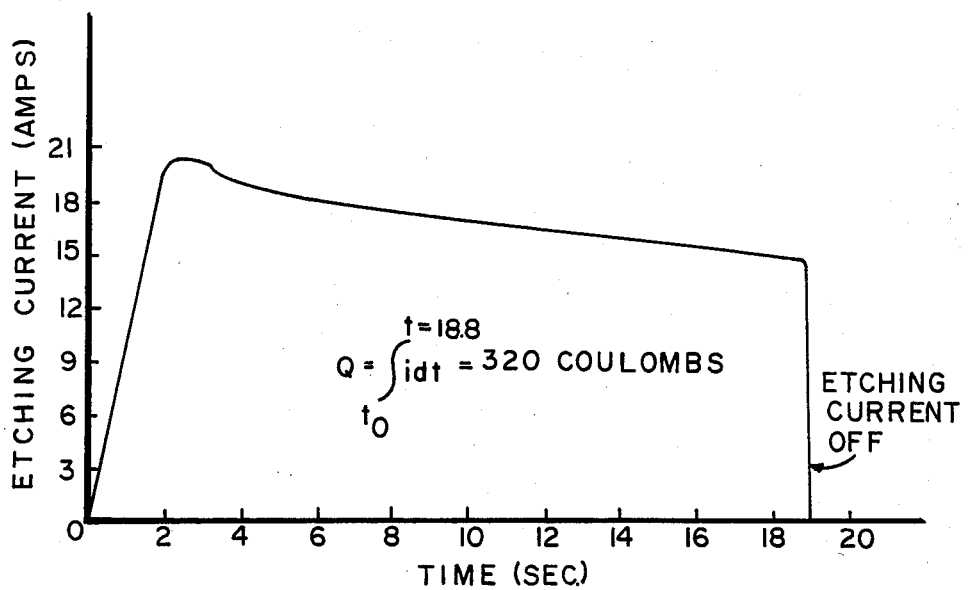
FIG. 6 is a graph of etching current vrs. time for a typical analysis cycle using the system of the present invention.

Resistors 24 and 26 define a parallel current path through which all of the current through etching cell 40 flows with the combined value of the resistors being 0.05 ohms. The resistors each have a power rating of 25 watts and a tolerance of 1 percent. The wire wound resistors have a relatively low temperature coefficient and are commercially available high quality resistors. As seen in FIG. 6, the etching current through cell 40 averages approximately 16 to 20 amperes thereby providing a voltage drop of about 1 volt across resistors 24 and 26. This voltage which is directly related to the current flowing in the etching cell 40, together with the time of application, is the total charge supplied to electrolytically etch the specimen.

By actually measuring the current flowing through the etching solution via conductors 36 and 33, the exact charge applied to etch material from the metal specimen 45 can be determined. By integrating the current vrs. time curve, as shown in FIG. 6, by conventional software in the microprocessor 60, the selectable desired charge is known. When reached, relay 30 (K-1) is turned off and a known amount of material has been etched from the sample. Knowing the amount of material that is etched according to Faraday's Law permits the user to subsequently detect the percentage of the soluble aluminum by using a dyeing agent and a colorimeter to provide a detected signal corresponding to the color intensity caused by the percentage of soluble aluminum in the etching solution. The microprocessor 60 includes in memory a lookup table of detected voltages, for example, detected by the colorimeter for samples containing known amounts of soluble aluminum and compares the detected signal during each analysis with the stored information to provide an output signal for display by a display 66.

Figure 5:
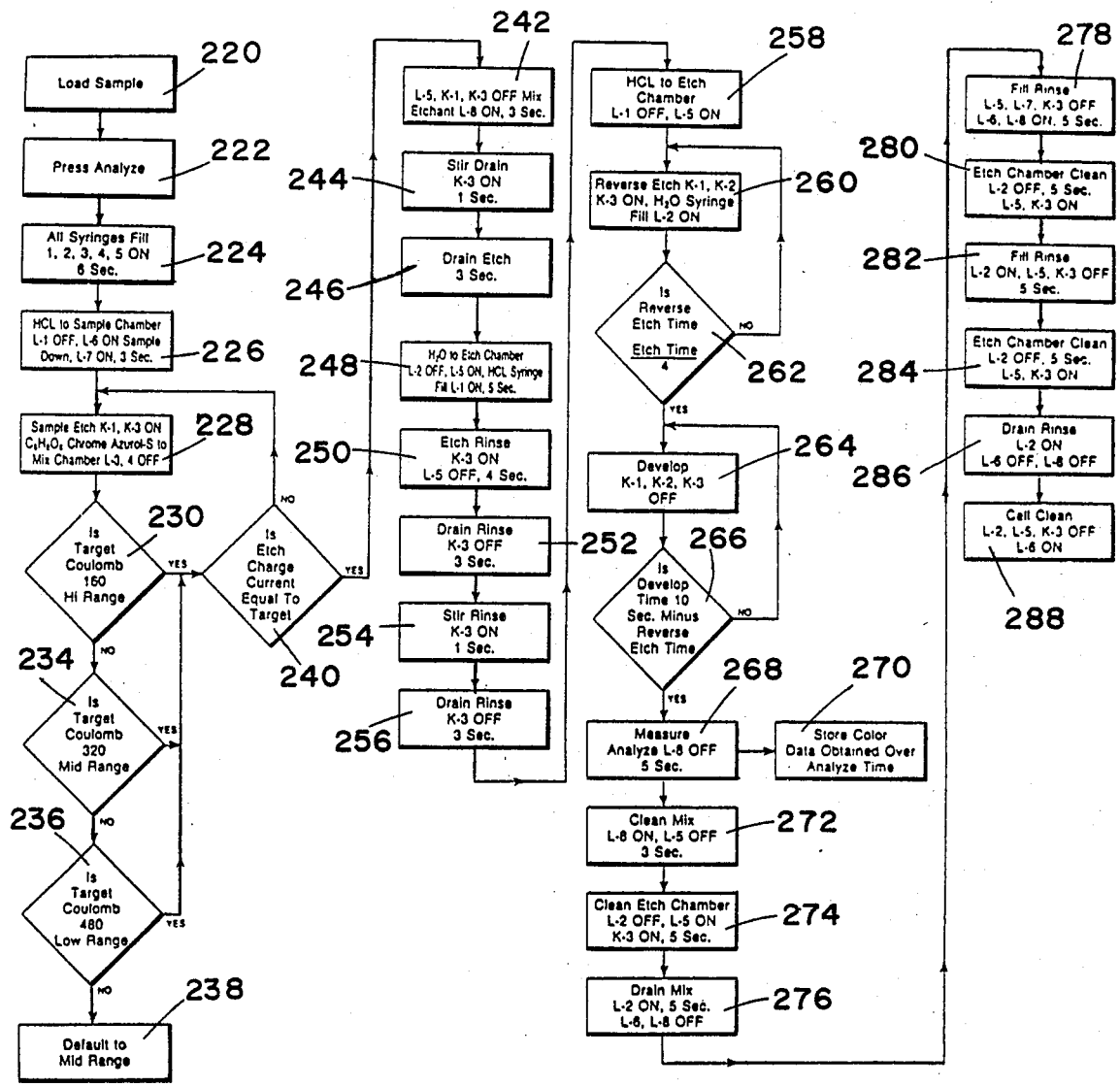
FIG. 5 is a flow diagram for the software employed for controlling the microprocessor and shows the sequence of operation of the system of the present invention.

The current representative voltage is measured by coupling the high input impedance terminals 52 and 54 of an analog-to-digital converter 50 across the resistors as shown in FIG. 1. The A/D converter 50 is controlled by a signal from an 8085-type microprocessor 60 applied to the A/D converter 50 via an interconnecting buss 56 in a conventional manner. The converter samples the voltage across resistors 24 and 26 approximately 16 times per second and converts the voltage information into a digital signal respresentative of the amplitude of the voltage and, therefore, the current flowing through resistors 24 and 26 and cell 40. This information is applied to a data input terminal 62 of the microprocessor via interconnecting conductors 58. As can be appreciated, the microprocessor 60 is coupled in a conventional way through a variety of interface circuits and drive circuits to provide other controlling functions for the analyzer disclosed herein and is programed according to the flow chart as shown in FIG. 5 to provide drive signals to the various operating solenoids and also to a relay drive circuit 65 in timed sequence. A control signal at time $t_o$, as seen in FIG. 6 for example, is applied to relay drive circuit 65 via conductor 64 to provide drive current to the coil 35 of relay 30 closing contacts 32 and 34 and initiating the etching of a disc-shaped sample 45.

The microprocessor continually monitors the etching current by converting the voltage sampled across resistors 24 and 26 to corresponding current integrating this sensed current with time until such time as, for example in FIG. 6, 320 coulombs of electrical charge have been applied to the specimen positioned between electrodes 42 and 44. At such time, the relay drive circuit 65 is deactivated by the microprocessor and approximately 80 milligrams of sample has been etched into solution from the disc-shaped solid metal sample 45. The fluid sample is, as will be described below in connection with FIGS. 2-4, transferred to a developing and mixing chamber 150 in which dye which bonds to the aluminum is applied to the solution and its color intensity measured to provide a readout on display 66, coupled to circuit 60 via conventional driver circuits. Display 66 displays the percentage by weight of acid-soluble aluminum in the steel sample. Thus, the circuitry shown in FIG. 1 provides digital information to microprocessor 60 of the actual etching current applied to the etching cell 40. It is to be understood that the current is not applied directly across the sample 45 but to one surface of the sample and to the lower electrode spaced from the sample and surrounded by the etching fluid as explained in connection with FIGS. 2-4 which are now described.

Figure 2:
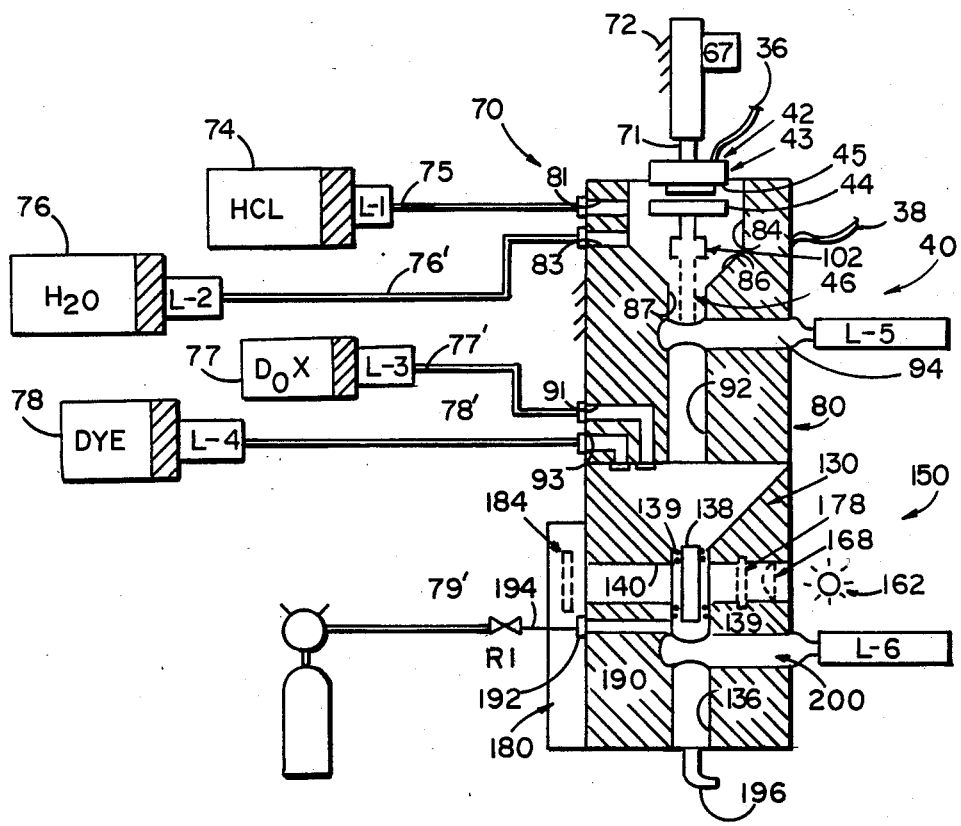
FIG. 2 is a pictoral diagram partly in cross section of the structure employed in connection with the present invention.
Figure 3:
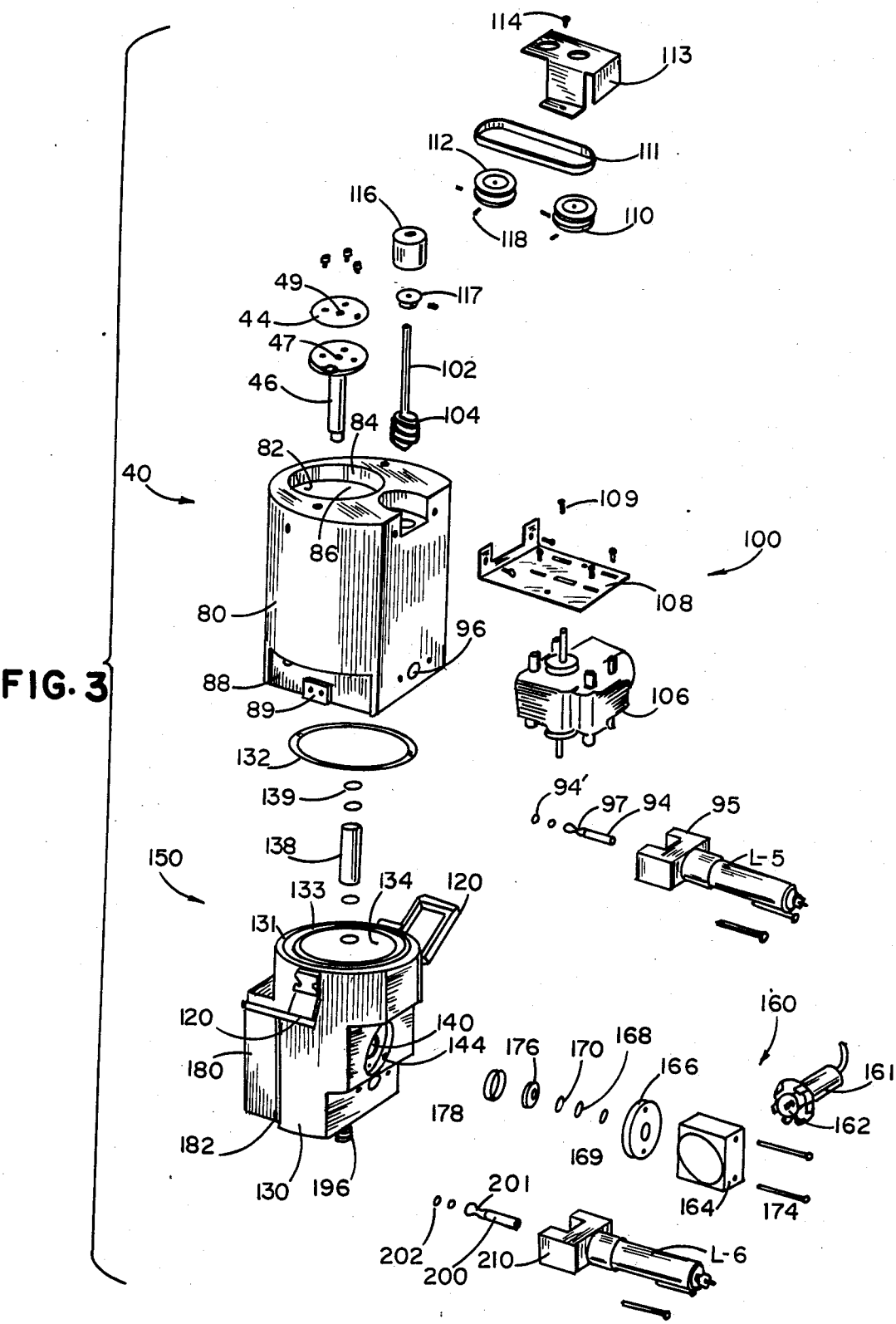
FIG. 3 is an exploded prespective view of a portion of the structure shown in FIG. 2.
Figure 4:
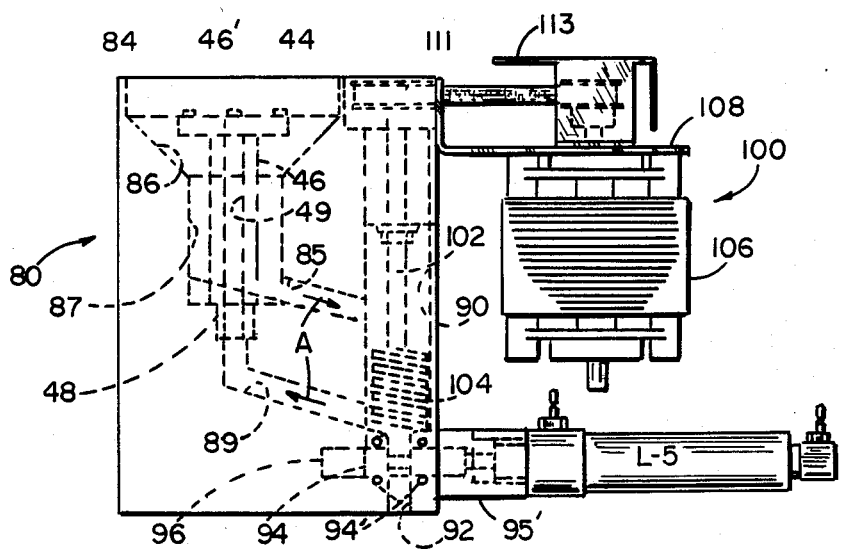
FIG. 4 is an assembled right side elevational view of the etching chamber shown also in FIG. 3.

Referring now to FIGS. 2-4, and initially FIG. 2, there is shown an analyzer 70 of the present invention which includes a cabinet 72, shown schematically in FIG. 2, for mounting the various components. The cabinet includes a separate section for mounting the electronics system shown in FIG. 1, and containers for four reagents comprising 0.25N hydrochloric acid, distilled water, a deoxidizing agent comprising ascorbic acid and sodium bisulfite and a dye comprising sodium acetate and chrome S azurol 78. These reagents are confined in supply vessels 74, 76, 77 and 78, respectively, shown schematically in FIG. 2. In practice, the vessels comprise bottles held within the cabinet 72 of the instrument.

Coupled to each of the bottles is an associated solenoid and syringe system shown pictorially in FIG. 2 as a cross-hatched section of the containers and the connecting solenoids L-1 through L-4. Each of the reagents are pumped into the analyzer, and particularly the electrolytic cell 40 and mixing chamber 100, by precise syringes. The syringes are each coupled through a check valve to one of the containers 74–78 with each of the reagents having its assigned separate syringe via interconnecting tubing and a check valve. Each of the dual acting electrically actuated solenoids L-1 through L-4 are pneumatically coupled to a syringe plunger and are controlled by microprocessor 60 through conventional interface circuits such that upon actuation in a first direction, the syringes draw liquids from their associated reagent container through the check valve into the syringe with the solenoids being actuated for a predetermined period of time and limited by stops to draw in a precise volume of reagent. Upon actuation in the opposite direction, the syringe forces the reagent outwardly through tubing such as tubing 75 associated with the hydrochloric acid 74 and into the etching cell 40.

In addition to the liquid reagents employed, a supply of nitrogen 79 is provided and is selectively applied to the mixing and developing chamber 150 by actuation of solenoid L-8 which provides the gas through a flow restrictor 79' maintaining the flow of nitrogen to 500 cc/min. The time sequence of operation of the reagents and gas supply 79 is controlled by the microprocessor and a stop for selectively filling the syringes to the precise amount desired and subsequently injecting the reagent into the analyzer 70 as will be described in greater detail below in connection with FIG. 5.

The analyzer employs a unique construction of vertically stacking etching cell 40 above and in alignment with the mixing and developing chamber 150, as seen in FIGS. 2 and 3. The etching chamber 40 supports the electrode assembly 43 which includes a disc-shaped upper electrode 42 typically made of an alnico magnet for removably holding the disc-shaped sample 45 of ferro-magnetic material thereto. The disc-shaped upper electrode 42 can be coated with an acid-resistant polymeric coating and conductor 36 is coupled thereto for supplying the electrical operating power to the electrode. The electrode is coupled to the shaft 71 of raising and lowering cylinder controlled by solenoid L-7 which raises the upper electrode 42 to a position providing an operator access for placing the sample in alignment with the electrode, as illustrated in FIG. 2, and lowering the electrode 42 such that the lower surface of sample 45 engages three insulated spacers 46' (FIGS. 3 and 4) holding the sample in predetermined spaced relationship above the platinum lower electrode 44 which is mounted on a hollow cylindrical pedestal 46. Pedestal 46 is supported by a recess 48 (FIG. 4) formed in the body 80 of cell 40. Pedestal 46 and electrode 44 each include a central longitudinally extending aligned apertures 47 and 49, respectively, permitting the upward flow of electrolytic solution which is circulated during etching and which flows in the space between the upper surface of lower electrode 44 and the lower surface of the specimen 45 in the space provided by the spacers 46'. Conductor 38 is electrically coupled to lower electrode 44 through the conductive cell body 80 and pedestal 46.

The etching chamber 40 is defined by body 80 having a downwardly cupped-shaped recess 82 open at its top end 81 permitting access for the movable upper electrode 42. The cabinet 72 typically encloses at least three sides of the body 80 and may include a vent positioned above the housing for venting any vapors associated with the etching process. The cup-shaped recess 82 includes a vertical cylindrical extending section 84 communicating with the top of the housing and an intermediate funnel-shaped inwardly and downwardly tapered section 86 whose lower end communicates with a reduced diameter downwardly depending cylindricaly section 87 which in turn communicates with cylindrical recess 48.

A fluid port 85 communicates with the lower end of the cylindrical section 87 and the annular space between the walls of cylindrical section 87 and the cylindrical pedestal 46 of the lower electrode, as best seen in FIG. 4, to drain the etchant material into a vertically extending cylindrical chamber 90 (FIG. 4) having a drain opening 92 at its lower end and including an outlet port 89 above a sliding valve 94 controlled by solenoid L-5. A recirculating pump assembly 100 includes a drive shaft 102 and impeller 104 at its lower end for circulating electrolytic solution with valve 94 in a closed position in a direction indicated by arrows A in FIG. 4.

The recirculating pump assembly 100 includes a pump motor 106 which is actuated by relay K-3 referred to in FIG. 5 and which is controlled by the microprocessor 60 through a suitable interface circuit (not shown). Motor 106 is coupled to body 80 by means of a bracket assembly 108, as best seen in FIGS. 3 and 4, which includes suitable fastening screws 109. The output shaft of motor 106 is coupled to a small-diameter drive pulley 110 which is coupled to a larger diameter drive pulley 112 spaced therefrom by means of a drive belt 111. A protective pulley guard 113 extends over the drive belt 111 and is fastened to mounting plate 108 by screws 114. An impeller bushing 116 is coupled to shaft 102 as is a slinger 117 positioned below bushing 116. The end of drive shaft 102 is coupled to pulley 112 by means of a set screw 118 such that actuation of the motor 106 causes the circulation illustrated by arrows A in FIG. 4.

The body 80 of etching cell 40 also includes a transverse axially extending recess 96 into which the configurated plunger valve 94 extends. Valve 94, as best seen in FIG. 3, is coupled to solenoid L-5 through a cylinder block 95 with sealing rings 94' surrounding the plunger 94 (FIG. 4) to seal the plunger with respect to aperture 96. Plunger 94 includes a reduced diameter section 97 which when in a position, as indicated in FIG. 4, aligned within the cylindrical drain aperture 92 of cell 40 permits the etchant fluid to flow downwardly therethrough. When activated to a closed position, the plunger valve 94 moves to the left, as illustrated in FIG. 4, such that the larger diameter portion of the plunger fills and seals the drain 92.

The lower end of housing 80 includes flattened side walls 88 to which are mounted the plates 89 of rim latch assemblies including latching member 120 mounted to the body 130 of the mixing and developing chamber 150 such that the units housing 80 and 130 can be disassembled. The lower surface of housing 80 is flat and is sealably secured to the upper surface 131 of mixing chamber 150 by means of an O-ring seal 132 which fits within an annular groove 133 formed downwardly through the annular top surface 131 of body 130. As best seen in FIG. 2, body 80 also includes a port 81 communicating with tube 75 and within the space defined by side walls 84 and 86 of the etching chamber for providing a flow path of hydrochloric acid into the chamber near the top thereof. Similarly, a port 83 is provided below port 81 for receiving a fitting and the water flow tube 76'. A pair of L-shaped ports 91 and 93 are formed through the bottom and side walls of body 80, as best seen in FIG. 2, for providing a flow path for the deoxidizing agent through tube 77' and the dye through tube 78' with ports 91 and 93 having outlets directed above the funnel-shaped mixing and developing chamber 150.

The body 130 of the mixing and developing chamber 150 includes a downwardly funnel-shaped aperture 134 extending downwardly from the top surface 131 terminating at its lower end in a cylindrical aperture 136 (FIG. 2) which receives a transparent detector tube 138 sealed at opposite ends by a pair of O rings 139 as best seen in FIG. 2. The O rings and detector tube seal a transversely extending port 140 from the fluid flow path at the interior of the mixing and developing chamber 150.

Mounted to one side of port 140 within annual recess 144 (FIG. 3) surrounding port 140 is a light and filter assembly 160 comprising a bulb holder 161 having a bulb 162 therein for providing illumination through the port 140 and the dyed etchant material contained within the detector tube 138. Bulb holder 161 fits within a light holding mount 164 which is secured to a lens holder 166 in which a lens 168 is mounted between O rings 169 and 170. Screws 172 secure holder 162 and lens holder 166 to body 130 through suitable mounting apertures therein. A spacer washer 176 extends between lens 170 and a blue light-transmissive filter 178 which passes blue light having a wavelength of about 545 nm therethrough. Thus, illumination from lamp 162 is limited to the spectrum of interest with respect to the dyed etchant solution and is transmitted through detector tube 138 containing the material onto a detector assembly 180 which is secured to the mixing chamber body 130 by means of a gasket 182. The detector assembly 180 includes, as best seen in FIG. 2, a light detecting photo diode 184 which receives light whose intensity is inversely related to the percentage by weight of acid-soluble aluminum in the etchant material contained within detector tube 138. The photo diode 184 is coupled to an input of microprocessor 60 through suitable interface circuitry such as an operational amplifier and A/D converter for providing signals to the microprocessor representing the intensity of light detected and thereby the amount of acid-soluble aluminum in the etchant solution. The mixing and developing chamber 150, as seen in FIG. 3, can be removed and lowered from the etchant cell 40 by the use of the rim latches 120 on either side of the generally cylindrical body 130. This may be desirable for purposes of servicing the light or lens assembly, detector tube, etc.

Below the detector tube 138 there is provided an axial passageway 190 extending into the cylindrical channel 136 above sliding valve 200. Port 190 is threaded to receive a fitting 192 coupling an air tube 194 from flow regulator 79' to the interior volume of the mixing and detector chamber 150 for allowing the nitrogen from supply 79 when valve L-8 is actuated by microprocessor 60 to bubble upwardly through the detector tube providing mixing of the etchant fluid and the dye and deoxidizing agents injected into the funnel-shaped interior chamber through ports 91 and 93. This assures a homogeneous mixture and uniform color denisty of the detected chemical mixture.

The end of cylindrical channel 136 below valve 200 terminates in a drain 196. Valve 200, like valve 94, includes a central restricted section 201 (FIG. 3) providing the valve open or closed operation with movement of the valve 200 by solenoid L-6. Valve 200 is mounted to the housing 130 by means of a mounting plate 210, as best seen in FIG. 3, with suitable 0 rings 202 mounted therein to provide sealed operation. The mounting of valve 200 to selectively obstruct the drain opening 196 and its mounting to the body 130 is substantially the same as the mounting and construction of valve 94 with respect to housing 80 as shown in detail in FIG. 4.

The sequence of operation of the system shown in FIGS. 1–4 can best be understood by reference to the flow diagram of the program for the microprocessor and which provides a sequence of operation for the system. The sequence of an analysis is initiated by the loading of the sample indicated by block 220 which is accomplished with L-7 in a raised position such that a prepared specimen 45 can be manually placed on the magnetic upper electrode 42 and held in place thereon. The specimen is disc shaped and can have a diameter of from about 0.75–2.125 inches and a thickness from about 0.25–2 inches. An analyze push-button switch is located on the analyzer 70 and is then actuated by an operator as indicated in step 222 to initiate the automatic microprocessor controlled sequence. Initially, the syringes associated with the reagents are filled as discussed above by the actuation of solenoids L-1–L-4 for a period of about 6 seconds as indicated by block 224. L-5 is also actuated to shut the drain 92 from the etching chamber so that fluid introduced into the etching chamber will remain in the etching chamber during etching. As indicated by block 226, the dilute hydrochloric acid is injected by the actuation of L-1 which actuates the syringe in the reverse direction pumping the dilute hydrochloric acid through tubing 75 and port 81 of the etching chamber 40 into the interior space of the etching chamber. The lower drain valve 200 is closed by the actuation of solenoid L-6, and L-7 is actuated to lower the sample onto the insulated spacer blocks 46'.

Next, as indicated by block 228, the microprocessor provides a control signal to relay drive circuit 65 (FIG. 1) to activate etching current relay K-1 and at the same time the stirring motor 106 through the actuation of its controlling relay K-3. At this point in time, the etch fluid flows upward and then between electrodes 44 and 45, and the microprocessor begins monitoring the current, as seen in FIG. 6, integrating it with time. Also during this time period, L-3 and L-4 are actuated to inject the reagents into the lower mixing and developing chamber from supply 77 and 78. As the etching and etchant solution circulation takes place in the etching chamber, the microprocessor checks, as indicated in blocks 230, 232 and 234, as to whether high, mid- or low range of charge has been selected. The analyzer provides three ranges varying from 160, 320 or 480 coulombs depending on the amount of aluminum expected to be in the sample. Thus, with a lower amount of aluminum content in the sample, it is necessary to etch for a longer period of time and thereby apply a greater amount of charge to the etching cell 40. Thus, with an aluminum content of, for example, 0.002 percent by weight or slightly above, the 480 range would be selected. Typically, the mid-range is selected and, in the event the operator has not selected a particular range, the program, as indicated in block 238, defaults as indicated by block 230 to the mid-range test 234.

Once the etch charge is reached as detected by the comparison step indicated by block 240, the etching process is stopped by the activation of K-1 to disconnect the power supply 16 from the cell 40 as indicated by block 242. The other functions indicated in block 242 and the solenoid table also take place at this time.

As the etchant is drained, as indicated by block 244, the stirrer is actuated for a short period of time with the drain being allowed to remain open for a period of time as indicated by block 246. Subsequently, as indicated by block 248, distilled water from vessel 76 and its associated syringe is injected into the etching chamber through tube 76' and port 83 by the actuation of L-2 to an off position, and the etch drain 92 is closed by the actuation of L-5. At the same time, the hydrochloric acid syringe refills by the actuation of L-1. The distilled water is then circulated by the mixing pump impeller 104 by the actuation of motor 106 by turning K-3 on as indicated by block 250. The flushing of the remaining etchant solution in the etching chamber continues through blocks 252, 254 and 256 until the etching chamber wash solution has been flushed through the etching chamber and drained into the lower mixing chamber 150. At this time, valve 94 is closed by the actuation of L-5, as indicated by block 258, and the system cycles through a reverse etching process to clean the lower electrode 44.

Thus, the hydrochloric acid from vessel 74 is injected into the etching chamber which is now isolated from the previous etching fluid by the closure of valve 94. Reverse etching is achieved by the actuation of relays K-1 and K-2, with relay K-2 reversing the polarity on upper electrode 42 such that it is now coupled to the negative polarity of supply voltage with the lower electrode coupled to the positive voltage. During this time period, the water syringe is refilled as indicated also on block 260. After the reverse etch timer has timed out, as indicated by block 262, the etchant solution previously allowed to flow by gravity downwardly into the mixing and developing chamber 150 is allowed to developed during the reverse etching as indicated by blocks 264 and 266. Once the development has been accomplished for up to 10 seconds, during which nitrogen is bubbled through the mixing and developing chamber at a rate of 500 cc. per minute determined by flow restrictor 79', the nitrogen bubbling supply is turned off. Sensor 184 detects the intensity of light and, therefore, provides a signal to the microprocessor representative of the percent-by-weight of acid-soluble aluminum present in the sample as indicated by block 268. This information is stored in the microprocessor and displayed to the instrument operator as indicated by block 270.

The mixing chamber is then cleaned by the dumping of the reverse etch solution into the mixing chamber, as indicated by block 272, and the introduction of water into the etching chamber, as indicated by block 274, with the drain 94 turned off while stirring through the actuation of motor 106 by K-3. Next, the etch drain is opened and the flushing water for the etching chamber is drained into the mixing chamber, as indicated by block 276, and a full rinse cycle is initiated in which a dual cycle of water flushing takes place as indicated by blocks 278 through 288. The analyzer then is ready for the admission of another sample and another analysis cycle. Typically, a complete cycle for the analysis of a sample takes less than 2 minutes with FIG. 6 representing the typical etching time period for the mid-range etching target of about 19 seconds.

By providing the vertically stacked etching and mixing and developing chambers, as illustrated in FIGS. 2 and 3, the system efficiently handles the reagent for the etching, reverse etching, cleaning, mixing and developing, and analyzing stages of operation without the necessity to pump etching solution and rinsing solution from one chamber to another. Thus, all that is necessary is to introduce the reagents into the respective chambers through the ports shown in FIG. 2, then sequentially operate the drains for each of the chambers.

The result is a relatively compact system which, with the current sensing provided by the electrical control circuit, precisely measures the amount of charge applied to the etching solution and, therefore, the weight of the sample dissolved. Thus, the analyzer of the present invention provides a rapid and accurate analysis for use typically in connection with the manufacturing of steel to determine the acid-soluble content of an aluminum and a steel sample.

It will be come apparent to those skilled in the art that various modifications to the preferred embodiment of the invention can be made without departing from the spirit or scope thereof as defined by the appended claims.

The embodiments of the invention in which an exclusive property or privilege is claimed are defined as follows:

1. Apparatus for handling an etching fluid for the electro-chemical analysis of a sample comprising:
   an etching cell for receiving a sample and applying an etching current to the sample through an etching fluid, said cell having an inlet for etching fluid and an outlet for draining the etching fluid from said cell;
   a mixing and developing chamber positioned below said etching cell and having an inlet coupled to said outlet of said etching cell for receiving etching fluid therefrom wherein said mixing and developing chamber further includes a colorimeter for determining the concentration of a sample material, said colorimeter including a light-transmissive channel extending across a portion of the chamber and a light source positioned on one side of said portion of said chamber and a light detector at the opposite side of said portion for directing light through etching fluid in said portion; and
   valve means coupled to one of said etching cell or chamber for selectively controlling the flow of etching fluid from said cell into said chamber.

2. The apparatus as defined in claim 1 wherein said mixing and developing chamber is axially aligned below said etching cell.

3. The apparatus as defined in claim 2 wherein said mixing and developing chamber includes means for removably mounting said mixing and developing chamber to said etching cell.

4. The apparatus as defined in claim 3 wherein said mixing and developing chamber includes a drain for said etching fluid and valve means selectively restricting said drain.

5. The apparatus for handling an etching fluid for the electro-chemical analysis of a sample comprising:
   an etching cell for receiving a sample and applying an etching current to the sample through an etching fluid, said cell having an inlet for etching fluid and an outlet for draining the etching fluid from said cell; and
   a mixing and developing chamber positioned in axial alignment below said etching cell and having an inlet coupled to said outlet of said etching cell for receiving fluid therefrom, wherein said mixing and developing chamber includes means for removably mounting said mixing and developing chamber to said etching cell and wherein said mixing and developing chamber includes a drain for said etching fluid and valve means selectively restricting said drain for selectively controlling the flow of etching fluid from said cell into said chamber; and wherein said mixing and developing chamber further includes a colorimeter for determining the concentration of a sample material, said colorimeter including a light-transmissive channel extending across a portion of the chamber and a light source positioned on one side of said portion of said chamber and a light detector at the opposite side of said portion for directing light through etching fluid in said portion.

6. The apparatus as defined in claim 5 wherein said mixing and developing chamber further includes a transparent cylindrical tube extending through said portion of said chamber and sealing means extending between said tube and said chamber to prevent fluid from contacting said light source or said light detector.

7. An electrical circuit for use in the electro-chemical analysis of a sample comprising;
   a power supply for supplying a direct current voltage;
   means for selectively coupling said power supply to electrodes of an etching cell;

current sensing means coupled to said power supply for determining the current flowing from said power supply through said etching cell; and circuit means coupled to said current sensing means and to said coupling means for controlling said coupling means as a function of the integral of current sensed with time.

8. The circuit as defined in claim 7 wherein said current sensing means comprises resistor means coupled in series with the current flow path of etching current supplied by said power supply.

9. The circuit as defined in claim 8 wherein said circuit means includes an analog-to-digital converter having input terminals coupled to said resistor means for sensing the voltage across said resistor means and a microprocessor coupled to an output of said analog-to-digital converter for receiving a digital signal therefrom representative of the etching current.

10. The circuit as defined in claim 9 wherein said microprocessor is coupled to analog-to-digital converter for sampling the voltage across said resistor means at a periodic rate and integrates the current sensed with time for generating a control signal applied to said coupling means for terminating etching current flow to the etching cell when a predetermined charge is reached.

11. An analyzer for determining the acid-soluble content of a sample comprising:

a power supply for supplying an etching current;

an etching cell having electrode means coupled to said power supply, said etching cell having an inlet for receiving an etching fluid and an outlet for said etching fluid;

circuit means coupled to monitor and control etching current supplied to said electrode means;

a mixing and developing chamber positioned below said etching cell and having an inlet coupled to said outlet of said etching cell for receiving etching fluid therefrom; and valve means coupled in the flow path of fluid flow between said etching cell and mixing and developing chamber for selectively controlling the flow of etching fluid into said chamber.

12. The analyzer as defined in claim 11 wherein said mixing and developing chamber is axially aligned below said etching cell.

13. The analyzer as defined in claim 12 wherein said mixing and developing chamber includes means for removably mounting said mixing and developing chamber to said etching cell.

14. The analyzer as defined in claim 13 wherein said mixing and developing chamber includes a drain for said etching fluid and valve means selectively restricting said drain.

15. The analyzer as defined in claim 11 wherein said circuit means includes resistor means coupled in series with the etching current flow path for developing a voltage directly proportional to the etching current.

16. The analyzer as defined in claim 15 wherein said circuit means includes an analog-to-digital converter having input terminals coupled to said resistor means for sensing the voltage across said resistor means and a microprocessor coupled to an output of said analog-to-digital converter for receiving a digital signal therefrom representative of the etching current.

17. The analyzer as defined in claim 15 wherein said microprocessor is coupled to said analog-to-digital converter for sampling the voltage across said resistor means at a periodic rate and integrates the current sensed with time for generating a control signal when a predetermined charge has been reached.

18. The analyzer as defined in claim 17 wherein said circuit means includes controlled switch means coupling said power supply to said electrode means and responsive to said control signal from said microprocessor to selectively couple said power supply to said electrode means for applying a predetermined charge to a sample.

19. An analyzer for determining the acid-soluble content of a sample comprising:

a power supply for supplying an etching current;

an etching cell having electrode means coupled to said power supply, said etching cell having an inlet for receiving an etching fluid and an outlet for said etching fluid;

circuit means coupled to monitor and control etching current supplied to said electrode means;

a mixing and developing chamber axially aligned below said etching cell and having an inlet coupled to said outlet of said etching cell for receiving etching fluid therefrom, wherein said mixing and developing chamber includes means for removably mounting said mixing and developing chamber to said etching cell and wherein said mixing and developing chamber includes a drain for said etching fluid and valve means selectively restricting said drain for selectively controlling the flow of etching fluid into said chamber; and wherein said mixing and developing chamber further includes a colorimeter for determining the concentration of a sample material, said colorimeter including light-transmissive channel extending across a portion of said chamber and a light source positioned on one side of said portion of said chamber and a light detector at the opposite side of said portion for directing light through etching fluid in said portion.

20. The analyzer as defined in claim 19 wherein said mixing and developing chamber further includes a transparent cylindrical tube extending through said portion of said mixing and developing chamber and sealing means extending between said tube and said chamber to prevent fluid from contacting said light source or said light detector.

* * * * *